(12) United States Patent
Ben-Shalom et al.

(10) Patent No.: US 6,589,942 B1
(45) Date of Patent: Jul. 8, 2003

(54) CHITOSAN METAL COMPLEXES AND METHOD FOR CONTROLLING MICROBIAL GROWTH ON PLANTS USING SAME

(75) Inventors: Noach Ben-Shalom, Tel-Aviv (IL); Riki Pinto, Colon (IL)

(73) Assignee: State of Israel, Ministry of Agriculture (IL)

( * ) Notice: Subject to any disclaimer, the term of this patent is extended or adjusted under 35 U.S.C. 154(b) by 324 days.

(21) Appl. No.: 09/621,915

(22) Filed: Jul. 24, 2000

Related U.S. Application Data

(63) Continuation of application No. 09/200,399, filed on Nov. 24, 1998, now abandoned.

(51) Int. Cl.⁷ ............... A01N 43/04; A01N 43/16
(52) U.S. Cl. ............... 514/55; 504/118; 504/292; 536/56
(58) Field of Search ............... 536/56; 514/55; 504/118, 242

(56) References Cited

U.S. PATENT DOCUMENTS

| | | | |
|---|---|---|---|
| 4,285,819 A | 8/1981 | Yen et al. | 210/679 |
| 4,536,207 A | 8/1985 | McCandliss et al. | 71/88 |
| 4,946,870 A | 8/1990 | Partain, III et al. | 514/777 |
| 4,970,150 A | 11/1990 | Yaku et al. | 435/101 |
| 4,971,956 A | 11/1990 | Suzuki et al. | 514/55 |
| 5,010,181 A | 4/1991 | Coughlin | 536/20 |
| 5,068,105 A | 11/1991 | Lewis et al. | 424/93 |
| 5,268,174 A * | 12/1993 | Sakuma et al. | 423/308 |
| 5,312,908 A | 5/1994 | Nakao | 536/20 |
| 5,374,627 A | 12/1994 | Ito et al. | 514/55 |
| 5,541,233 A * | 7/1996 | Roenigk | 106/122 |
| 5,643,971 A | 7/1997 | Roenigk | 523/122 |

FOREIGN PATENT DOCUMENTS

JP    06279219    * 10/1994

OTHER PUBLICATIONS

Kobashi et al., Bokin Bobai, vol. 24(3), pp. 191–193, abstract, 1996.*

* cited by examiner

*Primary Examiner*—James O. Wilson
*Assistant Examiner*—Howard V. Owens, Jr.
(74) *Attorney, Agent, or Firm*—Gifford, Krass, Groh, Sprinkle, Anderson & Citkowski, P.C.

(57) ABSTRACT

A method for controlling bacterial and fungal diseases in plants which includes applying a chitosan metal chelate complex having at least two metal ion species to the plant. Chitosan metal complexes for application to control bacterial and fingal diseases in plants are also disclosed.

11 Claims, No Drawings understood# CHITOSAN METAL COMPLEXES AND METHOD FOR CONTROLLING MICROBIAL GROWTH ON PLANTS USING SAME This application is a continuation of application No. 09/200,399, filed Nov. 24, 1998, now abandoned.

FIELD OF THE INVENTION

The present invention relates to agricultural compositions for delivering metals to plants and for controlling microbial diseases in plants. Specifically, the present invention relates to metals chelated with a particular carbohydrate-derived composition and to methods for its use in delivering metals to agricultural crops and in controlling microbial damage to agricultural crops.

BACKGROUND OF THE INVENTION

Historically, microbiological infestations have caused significant losses to agricultural crops and have been the cause of large scale famines and economic displacements. Fungal infections can cause pre-harvest damage to crops by killing them outright or by weakening them so as to decrease yields and render the plants susceptible to other infections. Post-harvest, fungal infections can also result in significant loss of agricultural products during storage, processing, and handling. The need for the control of microbial infections of agricultural products is well established and a number of chemical agents have been developed for this purpose, however, to date, no fully satisfactory chemical agents have been found. Oftentimes, fungal control agents are highly toxic to crops and/or animals; consequently, restrictions are placed on their handling and use. Also, many presently available fungal control agents are of restricted utility; that is to say, a particular agent may be effective only against several types of fungus. As a result, a number of separate materials must often be employed in a particular agricultural setting in order to accommodate different types of fungi or other microbial pathogens. Also, as is common with anti-microbial agents, a number of fungal species have developed resistance to commonly employed fungicides.

Clearly, there is a need for an anti-microbial control agent which can be utilized for both bacterial and fungal agents in plants which has broad activity against a variety of fungi and bacteria including those strains resistant to presently employed fungicides. Ideally, the material should be of low toxicity to crops and to animals, stable in composition, easy to employ, and preferably low in cost.

It is well known that the cell walls of fungi are comprised of chitin, which is a natural, carbohydrate-based biopolymer. Chitin is an analog of cellulose in which the OH group at the C-2 position has been replaced by an acetamido group. Chitin is also abundantly found in a number of natural sources, including the shells of arthropods such as shrimp. Previous research has suggested that chitin, or lower molecular weight fractions produced by its degradation, can in some instances, elicit antifungal responses in some plants, see for example, M. G. Hahn et al. in *Mechanisms of Plant Defense Responses*; B. Fritig and M. Legrand, Kluwer Academic Publishers (Netherlands 1993, pp. 99–116).

Chitosan is a semi-synthetic derivative of chitin produced by the deacetylation of the nitrogen thereof so as to produce the ammonium salt. Chitosan itself has been shown to have some mild antifungal activity with regard to certain particular fungal species in some particular plants, see for example, L. A. Hadwiger, J. M. Beckman; *Plant Physiol.*, 66, 205–211 (1980); A. El Gharouth et al., *Phytopathology*, 84, 313–320 (1994); A. El Gharouth et al., *Phytopathology*, 82, 398–402 (1992); C. R. Allan et al., *Experimental Mycology*, 3:285–287 (1979); and P. Stossel et al., *Phytopathology Z.*, 111:82–90 (1984). Specific hydrozylates of chitosan have also been described as having some antifungal activity. See for example, Kendra et al., *Experimental Mycology*, 8:276–281 (1984). U.S. Pat. No. 5,374,627 discloses the use of a composition of high molecular weight chitosan hydrozylate (M.W. 10,000–50,000) and acetic acid for controlling fungus in certain crops. Japanese Patent Application 62-198604 describes the use of very low molecular weight chitosan hydrozylates (M. W. $\leq$3,000) for the control of *Alternaria alternata* fungus in pears. It is further noted that this material is not effective, in pears, against other fungi such as Botrytis.

The ability of chitosan to form complexes with metal ions, particularly of the transition metals and post transition metal ions, is well known in the literature, see generally George A.F. Roberts, *Chitin Chemistry*, Macmillan (1992). Most of the work described in this publication was done with the insoluble form of the chitosan metal complexes dealing with different ion interactions and the type of complex formation. Almost none of the work dealt with the soluble complex formation and no suggestion was made for the use of chitosan metal complexes for use in agriculture.

U.S. Pat. No. 5,010,181 to Coughlin also discloses the use of chitosan for removing heavy metal ions from aqueous solution.

U.S. Pat. Nos. 5,643,971 and 5,541,233 both to Roenigk disclose the use of chitosan as a chelating polymer capable of forming coordinate bonds with transition metals. These metal complexes were utilized in a water-absorbing porous article, such as a sponge, in order to impart anti-microbial activity. Neither of the patents to Roenigk disclose the use of chitosan metal chelates for agricultural uses including the delivery of metal ions to plants and the use of chitosan metal chelates as anti-microbial agents against plant diseases. Accordingly, the present invention, as will be described in detail below, is directed to anti-microbial agents and/or metal delivery agents derived from chitin and/or chitosan and their methods of use in agriculture. This invention has identified particular chitosan metal chelate combinations which are particularly effective anti-microbial agents at very low doses. The material of the present invention is derived from natural sources and has extremely low toxicity to animals and agricultural crops. In addition, the material is stable, easy to handle, and low in cost. These and other advantages of the present invention will be readily apparent from the discussion, description, and examples which follow.

SUMMARY OF THE INVENTION

There is disclosed herein a method for delivering metal to plants. The method comprises combining a metal ion with chitosan to form a metal chelate complex and applying the metal chelate complex to a plant in order to deliver the metal to the plant.

There is also disclosed a chitosan metal complex comprising a chitosan chelating polymer and at least one different metal ions chelated to the chitosan chelating polymer. In a preferred embodiment, copper, zinc, and aluminum are all chelated to the chitosan chelating polymer.

Also disclosed are compositions containing chitosan metal complexes which include both a water soluble chitosan metal ion chelate and a water insoluble chitosan metal ion chelate.

Also included within the scope of the present invention are methods for treating microbial disease in plants which comprise applying the compositions of the present invention to plants either pre-harvest or post-harvest.

Also disclosed herein are soluble chitosan metal compositions suitable for hydration and application to plants.

DETAILED DESCRIPTION OF THE INVENTION

In accordance with the present invention, it has been found that particular oligomeric and/or polymeric materials derived from chitin or chitosan, having a molecular weight in the range of 4,000 to 500,000 daltons and comprised of linked, beta-glucosamine repeat units, is a highly effective chelating agent for transition metals thereby forming a highly effective agent for the control of a broad range of microbial diseases including bacterial and fungal diseases in a variety of plants.

Two different molecular weight chitosan polymer fractions can be utilized in the present invention. A first chitosan polymer fraction having a molecular weight ranging from approximately 10,000 daltons to approximately 500,000 daltons is combined with a second chitosan polymer fraction having a molecular weight ranging from approximately 4,000 daltons to approximately 10,000 daltons. It was found that for use as an anti-bacterial agent, that only chitosan polymers with a molecular weight ranging from 4,000–10,000 daltons was effective.

The material is prepared by the hydrolysis of chitin or chitosan, typically by acidic or enzymatic cleavage of the polymeric material, through the oxygen linkages thereof.

The degree of acetylation of the chitosan material can range from approximately 0–40%. The chitosan material or polymer can be reacted with transition metals and post-transition metal ions. Preferably, the chitosan polymer is reacted with metals including copper, zinc, aluminum, and manganese. Each metal alone and/or combinations of the metals are present in a concentration ranging from approximately 10–1000 ppm. More preferably, the chitosan polymer is reacted with one or more metals, for example Cu, Zn, Mn, yielding a complex which has improved anti-microbial activity and even further reduced toxicity.

The formation of the chitosan metal complex is achieved by reacting the chitosan (preferably at room temperature) with the desired metal or metals. The chitosan and the metal or metals are preferably incubated for between 1–24 hours. Both water soluble and water insoluble complexes are formed during the incubation period and the ratio of the free metals, the soluble complexes, and the insoluble complexes change as a function of time and the type of metal and the anion. Both the water soluble and the water insoluble complexes are effective anti-microbial agents. The amount of metal chelated by the chitosan can be determined by atomic absorption analysis.

The chitosan metal complexes of the present invention are particularly effective as the chitosan acts to not only bind the composition to the plant, but also appears to allow for the sustained release of metals over a longer period of time. The ability to form both soluble and insoluble complexes with the chitosan, provides the ability to bind the chitosan metal complexes to the leaves of plants thereby preventing the complexes from being washed away from the plants while also binding the metals to the complex yields a safe composition which prevents the washing of the metals from the leaves and provides a sustainable slow release mechanism. That is, the chitosan binds or sticks the metals to the plant while at the same time also retaining the metals therein. Chitosan is used both for its ability to chelate metals and its ability to attach or bind the metals to an object such as a plant. Also, since the phytotoxicity of the transition metals in their complexed state is significantly reduced, the complexes can be used in neutral pH conditions. Additionally, the chitosan binder provides a buffer between the metals and the plants to prevent direct contact between the metal and the plants thus further avoiding the inherent phytotoxicity of the metals.

The chitosan metal complexes of the present invention can also be provided as a dry mixture comprising a dry water soluble form of chitosan (Natural Polymer, Inc., Raymond, Wash.) which is supplied with a dry metal compound. The dry mixture can then be added to a farmer's tank in the field and mixed with water to completely solubilized the dry mixture which can then be applied to plants by various techniques well known to those of ordinary skill in the art including spraying.

The interaction between the dry, water soluble chitosan and the metals has been found to be dependent on the anion compounded with the metal. A preferred anion has been found to be a gluconate salt which appears to have lower toxicity than other anions and which has a higher affinity to the chitosan as compared to nitrates, chlorides and acetates. The gluconate salts have also been shown to have minimum side effects when applied to plants both with and without chitosan.

The utility of the compositions and methods according to the present invention are shown below in the Examples section.

EXAMPLES

Example 1

A chitosan metal complex of the present invention was sprayed onto the leaves of a cucumber (Cucumis sativus) (CV) plant grown in plastic pots in a commercial greenhouse (Hishtil, Afula, Israel). Whole plants with two true leaves were sprayed with 0.1%–0.13% of the chitosan metal complex material. Control plants were sprayed with water. After 24 hours, plants were inoculated with the fungi or the bacteria ($10^5$). Inoculated plants were placed in a greenhouse at 100% humidity at 25° C. The plants were incubated for 96 hours at which point, the percent diseased leaf area was visually estimated and the disease severity was calculated as a disease index for the whole plant.

The control of the angular leaf spot disease caused by *Pseudomonas lacrimans* in cucumber leaves utilizing 0.1% chitosan and $CuNO_3$, $ZnNO_3$ and $AINO_3$ utilizing 15, 40, and 60 ppm each, in a ratio of 1:1:1 was utilized. As shown in Table I, plants treated with a chitosan metal complex controlled disease in an amount greater than the chitosan alone. Plants treated with multiple metals complexed with the chitosan displayed the most marked percentage of disease control.

TABLE I

| Treatments | Percent Control Disease |
|---|---|
| Cucumber + water | 0 |
| Cucumber + hydrolysed chitosan (HC) | 52 |
| Cucumber + HC + 15–60 ppm Cu | 75 |
| Cucumber + HC + 15–60 ppm Zn | 72 |

TABLE I-continued

| Treatments | Percent Control Disease |
|---|---|
| Cucumber + HC + 15–60 ppm Al | 62 |
| Cucumber + HC + 45 ppm Cu + Zn + Al | 56 |
| Cucumber + HC + 120 ppm Cu + Zn + Al | 83 |
| Cucumber + HC + 180 ppm Cu + Zn + Al | 95 |
| Cucumber + HC + 250 ppm streptomycin | 95 |

Example 2

Controlling the *Phytophtora infestans* disease in potato plants was demonstrated using 0.1% chitosan and $CuNO_3$ (100–200 ppm). As shown in Table II, the chitosan metal complexes were shown to be highly effective in controlling the *Phytophtora infestans* organism. Furthermore, the chitosan chelated copper complex was shown to be much less toxic than the copper compound applied directly to the potato leaves.

TABLE II

| Treatments | Percent Control Disease |
|---|---|
| Potato leaves + water | 0 |
| Potato leaves + chitosan | 75 |
| Potato leaves + chitosan + 100 ppm metals | 85 |
| Potato leaves + chitosan + 150 ppm metals | 95 |
| Potato leaves + chitosan + 200 ppm metals | 85 |
| Potato leaves + $CuNO_3$ + 25 ppm metals | toxic |
| Potato leaves + $CuNO_3$ + 50 ppm metals | toxic |
| Potato leaves + $CuNO_3$ + 75 ppm metals | toxic |

Example 3

Controlling Downy mildew disease caused by *Pseudoperonospera cubensis* in cucumber plants was demonstrated utilizing 0.1% chitosan and $CuNO_3$ (100–200 ppm).

As shown in Table III, the chitosan copper complex controlled the Downy mildew diseased caused by *Pseudoperonospera cubensis* in cucumber plants. Furthermore, the chitosan copper complex was shown to be much less toxic to the cucumber plants as opposed to the direct application of the copper nitrate itself.

TABLE III

| Treatments | Percent Control Disease |
|---|---|
| Cucumber + water | 0 |
| Cucumber + chitosan | 65 |
| Cucumber + chitosan + 100 ppm metals | 80 |
| Cucumber + chitosan + 150 ppm metals | 90 |
| Cucumber + chitosan + 200 ppm metals | 85 |
| Cucumber + $CuNO_3$ + 25 ppm metals | toxic |
| Cucumber + $CuNO_3$ + 50 ppm metals | toxic |
| Cucumber + $CuNO_3$ + 75 ppm metals | toxic |

Example 4

Controlling the bacterial spot disease caused by *Xanthomonas campestris* in tomato plant leaves utilizing various metals.

As shown in Table IV, the chitosan metal complexes of the present invention controlled the bacterial spot disease caused by *Xanthomonas lacrimans* in tomato plants to a greater degree than did chitosan alone.

TABLE IV

| Treatments | Percent Control Disease |
|---|---|
| Tomato leaves + water | 0 |
| Tomato leaves + 0.1% chitosan | 10 |
| Tomato leaves + chitosan + 100 ppm Cu | 70 |
| Tomato leaves + chitosan + 100 ppm Cu + 100 ppm ZN | 70 |
| Tomato leaves + chitosan + 100 ppm ZN | 65 |
| Tomato leaves + chitosan + 100 ppm Cu + 100 ppm Mn | 45 |

Example 5

Controlling the Gray mold disease caused by *Botrytis cinerea* in cucumber plants utilizing 0.1% chitosan and metal complexes.

Referring to Table V, the chitosan metal complexes were shown to be at least as effective in the control of Gray mold disease as was chitosan alone. Furthermore, the chitosan metal complexes were shown to be non-toxic as compared with the application of the metal (copper nitrate) itself.

TABLE V

| Treatments | Percent Control Disease |
|---|---|
| Cucumber + water | 0 |
| Cucumber + 0.1% Hydrolysed chitosan (HC) | 84 |
| Cucumber + HC + 100 ppm Cu | 84 |
| Cucumber + HC + 100 ppm Zn | 83 |
| Cucumber + HC + Mn | 84 |
| Cucumber + $CuNO_3$ + 35 ppm metals | toxic |
| Cucumber + $CuNO_3$ + 50 ppm metals | toxic |

Example 6

Comparing the control of *Xanthomonas campestris* in tomato plant leaves using a complex of chitosan, copper and different anions (nitrate, acetate, and gluconate).

Referring to Table VI, the chitosan metal complexes of the present invention were shown to be effective in controlling *Xanthomonas campestris* in tomato plants. It is important to note that the gluconate salt was more effective at controlling disease than both the acetate and nitrate salts.

TABLE VI

| Treatments | Percent Control Disease |
|---|---|
| Tomato + water | 0 |
| Tomato + 0.1% chitosan | 10 |
| Tomato + chitosan + 100 ppm Cu acetate | 60 |
| Tomato + chitosan + 100 ppm Cu nitrate | 70 |
| Tomato + chitosan + 100 ppm Cu gluconate | 88 |

While the foregoing has been described with reference to some specific species, it is to be understood that the general principles presented hereinabove are applicable to the protection of a wide variety of agricultural crops from a broad spectrum of microbial agents. Also, while certain synthetic procedures for preparing the chitosan metal complexes of the present invention have been described, it is to be understood that a material may be prepared by many other routes which will be apparent to one of skill in the art. For example, other sources of chitosan or chitin may be employed for the preparation of the metal complexes, and such sources include cell walls of fungi, exoskeletons of various marine invertebrates, as well as exoskeletons of terrestrial arthropods. Likewise, the chitosan matrix may be obtained from various sources. In view thereof, it is to be understood that the foregoing discussion, description, and examples are illustrative of particular embodiments of the present invention, and are not meant to be limitations upon the practice thereof. It is the following claims, including all equivalents, which define the scope of the invention.

What is claimed:

1. A method for controlling bacterial and fungal diseases in plants by applying a composition comprising chitosan and at least two transition metal compounds to the plant, at least one of said transition metal compounds comprising a gluconate salt.

2. A method as set forth in claim 1, wherein the transition metal is selected from the group consisting of copper, aluminum, manganese, and zinc.

3. A method as set forth in claim 1, wherein three different metal ion species are combined with the chitosan.

4. A method as set forth in claim 1, wherein the metal chelate complex is water soluble.

5. A method as set forth in claim 1, wherein the metal chelate complex is water insoluble.

6. A method as set forth in claim 1, wherein the metal chelate complex includes both a water soluble fraction and a water insoluble fraction.

7. A method as set forth in claim 1, wherein the concentration of the metal ion in the metal chelate complex ranges from approximately 10 ppm to 1000 ppm.

8. A method as set forth in claim 1, wherein the chitosan comprises a mixture of a first chitosan polymer fraction having a molecular weight ranging approximately 10,000 daltons to approximately 500,000 daltons and a second chitosan polymer fraction having a molecular weight ranging from approximately 4,000 daltons to approximately 10,000 daltons.

9. A water soluble chitosan metal composition, said composition for controlling bacterial and fungal diseases in plants, said composition comprising:
   a dry, water soluble chitosan; and
   at least two transition metal compounds, at least one of said transition metal compounds comprising a gluconate salt.

10. A composition according to claim 9, wherein said transition metal is selected from the group consisting of copper, aluminum, manganese and zinc.

11. A method for controlling bacterial and fungal diseases in plants by applying to the plant a chitosan metal chelate complex comprising a mixture of a first, water insoluble, chitosan polymer fraction having a molecular weight ranging front approximately 10,000 daltons to approximately 500,000 daltons, said water insoluble fraction being chelated with a metal ion; and a second, water soluble, chitosan polymer fraction having a molecular weight ranging from approximately 4,000 daltons to approximately 10,000 daltons, said water soluble fraction being chelated with a metal ion; wherein at least one of said transition metal ions is present in a gluconate salt.

* * * * *